(12) United States Patent
Chang-Hasnain et al.

(10) Patent No.: US 10,330,602 B2
(45) Date of Patent: Jun. 25, 2019

(54) OPTICAL SENSOR USING HIGH CONTRAST GRATINGS COUPLED WITH SURFACE PLASMON POLARITON

(71) Applicant: THE REGENTS OF THE UNIVERSITY OF CALIFORNIA, Oakland, CA (US)

(72) Inventors: Connie Chang-Hasnain, Palo Alto, CA (US); Tianbo Sun, Berkeley, CA (US); Li Zhu, Richmond, CA (US); Fang Liu, El Cerrito, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/692,327

(22) Filed: Aug. 31, 2017

(65) Prior Publication Data

US 2018/0073987 A1  Mar. 15, 2018

Related U.S. Application Data

(63) Continuation of application No. PCT/US2016/021252, filed on Mar. 7, 2016.
(Continued)

(51) Int. Cl.
 *G01N 21/77* (2006.01)
 *G01N 21/552* (2014.01)
(Continued)

(52) U.S. Cl.
 CPC ....... *G01N 21/7743* (2013.01); *G01N 21/554* (2013.01); *G01N 21/648* (2013.01);
(Continued)

(58) Field of Classification Search
 CPC ................. G02B 6/00; G01N 21/77
(Continued)

(56) References Cited

U.S. PATENT DOCUMENTS

| 7,265,845 | B2 * | 9/2007 | Kochergin | G01N 21/553 |
| | | | | 324/244.1 |
| 7,436,596 | B2 * | 10/2008 | Robertson | G01N 21/553 |
| | | | | 359/587 |

(Continued)

OTHER PUBLICATIONS

Korean Intellectual Property Office (KIPO), International Search Report and Written Opinion dated May 27, 2016, related PCT International Application No. PCT/US2016/021252, pp. 1-16, with claims searched, pp. 17-20.
(Continued)

*Primary Examiner* — Kaveh C Kianni
(74) *Attorney, Agent, or Firm* — O'Banion & Ritchey LLP; John P. O'Banion

(57) ABSTRACT

An optical sensing platform with an array of sensors, a laser or broadband light source and an optical detector that utilizes surface plasmon resonance based transduction and optical detection is provided. The sensor structure of the platform has a low index support layer, a high contrast grating, a low index spacer and a thin metal film with a target recognition element. The surface plasmon resonance based sensor uses surface plasmon waves to detect changes on the surface of the sensor when a target interacts with the target recognition element. The binding of the target with a recognition element receptor will induce changes in the refractive index of the metal layer, which changes the resonance wavelength of the plasmon wave on the sensor surface, which is used to measure or observe the reaction.

6 Claims, 13 Drawing Sheets

Related U.S. Application Data

(60) Provisional application No. 62/129,763, filed on Mar. 7, 2015.

(51) Int. Cl.
*G01N 21/64* (2006.01)
*G02F 1/035* (2006.01)
*G02B 6/00* (2006.01)
*G01N 21/78* (2006.01)

(52) U.S. Cl.
CPC .............. *G02F 1/035* (2013.01); *G01N 21/78* (2013.01); *G01N 2021/7776* (2013.01); *G02F 2203/10* (2013.01)

(58) Field of Classification Search
USPC ........................................................ 385/130
See application file for complete search history.

(56) References Cited

U.S. PATENT DOCUMENTS

| | | | |
|---|---|---|---|
| 8,059,690 B2 | 11/2011 | Chang-Hasnain | |
| 8,189,643 B2 | 5/2012 | Chang-Hasnain | |
| 8,442,374 B2 | 5/2013 | Chang-Hasnain | |
| 8,488,646 B2 | 7/2013 | Chang-Hasnain | |
| 8,526,471 B2 | 9/2013 | Chang-Hasnain | |
| 8,755,118 B2 | 6/2014 | Chang-Hasnain | |
| 9,897,598 B2* | 2/2018 | Lakowicz | G01N 33/54373 |
| 2002/0021445 A1 | 2/2002 | Bozhevolnyi | |
| 2005/0014151 A1 | 1/2005 | Textor | |
| 2006/0211024 A1* | 9/2006 | Corn | B82Y 15/00 435/6.11 |
| 2006/0221343 A1 | 10/2006 | Bouhelier | |
| 2007/0115553 A1 | 5/2007 | Chang-Hasnain | |
| 2008/0007732 A1* | 1/2008 | Ja | G01N 21/6428 356/445 |
| 2008/0267555 A1* | 10/2008 | Kashyap | G01N 21/553 385/12 |
| 2009/0010589 A1* | 1/2009 | Robertson | G01N 21/553 385/12 |
| 2009/0052827 A1* | 2/2009 | Durfee | G02F 1/035 385/2 |
| 2011/0280269 A1 | 11/2011 | Chang-Hasnain | |
| 2012/0128019 A1 | 5/2012 | Chang-Hasnain | |
| 2012/0200959 A1 | 8/2012 | McCaslin | |
| 2013/0148194 A1* | 6/2013 | Altug | G01N 21/554 359/350 |
| 2014/0353530 A1 | 12/2014 | Chang-Hasnain | |
| 2014/0353583 A1 | 12/2014 | Chang-Hasnain | |
| 2015/0003220 A1* | 1/2015 | Peng | G11B 5/314 369/13.32 |
| 2015/0010034 A1 | 1/2015 | Chang-Hasnain | |
| 2015/0124254 A1* | 5/2015 | Page | G01N 21/553 356/369 |
| 2015/0286006 A1 | 10/2015 | Chang-Hasnain | |
| 2015/0288146 A1 | 10/2015 | Chang-Hasnain | |
| 2017/0023807 A1 | 1/2017 | Chang-Hasnain | |

OTHER PUBLICATIONS

Sugihwo, F. et al., "Simultaneous optimization of membrane reflectance and tuning voltage for tunable vertical cavity lasers", Appl. Phys. Lett. 72, 10 (1998), Jan. 5, 1998, pp. 10-12.

Sugihwo, Fred et al., "Low threshold continuously tunable vertical-cavity surface-emitting lasers with 19.1 nm wavelenght range", Appl. Phys. Lett. 70, 547 (1997), Feb. 3, 1997, pp. 547-549.

Sugihwo, Fredy et al., "Micromachined Widely Tunable Vertical Cavity Laser Diodes", Journal of Microelectromechanical Systems, vol. 7, No. 1, Mar. 1998, pp. 48-55.

* cited by examiner

OPTICAL SENSOR USING HIGH CONTRAST GRATINGS COUPLED WITH SURFACE PLASMON POLARITON

CROSS-REFERENCE TO RELATED APPLICATIONS

This application is a 35 U.S.C. § 111(a) continuation of PCT international application number PCT/US2016/021252 filed on Mar. 7, 2016, incorporated herein by reference in its entirety, which claims priority to, and the benefit of, U.S. provisional patent application Ser. No. 62/129,763 filed on Mar. 7, 2015, incorporated herein by reference in its entirety. Priority is claimed to each of the foregoing applications.

The above-referenced PCT international application was published as PCT International Publication No. WO 2016/144908 on Sep. 15, 2016, which publication is incorporated herein by reference in its entirety.

STATEMENT REGARDING FEDERALLY SPONSORED RESEARCH OR DEVELOPMENT

This invention was made with government support under N00244-09-1-0013 awarded by the Naval Post Graduate School. The government has certain rights in the invention.

INCORPORATION-BY-REFERENCE OF COMPUTER PROGRAM APPENDIX

Not Applicable

BACKGROUND

1. Technical Field

The present technology pertains generally to biological and chemical sensing devices and methods of use, and more particularly to an optical sensor based on a high contrast grating coupled with a surface plasmon polariton platform. The high contrast grating facilitates high optical coupling efficiency with a large tolerance of the interrogating optical beam with the surface plasmon polariton waves and improves the quality factor of the optical resonance, which in turn improves the sensitivity of the overall device.

2. Background Discussion

Laboratory assays such as, polymerase chain reaction (PCR), enzyme-linked immunosorbent assay (ELISA) and cell culturing methods are highly sensitive techniques that are available for the diagnosis of infectious diseases. However, these techniques require transportation of the sample to the lab, manual preparation steps, and skilled laboratory technicians to perform and read the assays. As a consequence, these techniques provide results in several hours to several days and are not capable of rapid detection. These techniques are also not capable of detecting or identifying multiple infectious agents such as bacteria and viruses at the same time.

Biosensors can provide label free detection of biomolecular or chemical interactions and have applications in medical diagnostics, environmental safety, bioterrorism, biomedical research and drug discovery. Generally, biosensors have an interaction sensing element that interacts with a target, a transducer that the transforms the sensed interaction into a readable optical, acoustic electrical, piezoelectric or similar signal and a read-out system to interpret the produced signal. The signal readout can be transformed into meaningful diagnostic information for a practitioner very quickly compared with existing assays.

Biosensors may be classified either by the type of biological sensing mechanism that is utilized or by the type of signal transduction that is employed. Typical biological signal mechanisms include a recognition element that is an immobilized biocomponent that is able to detect a specific target analyte.

Biological recognition mechanisms may include antibody/antigen, enzyme/substrate, nucleic acid sections and chemical adsorption or binding. The recognition mechanisms may also include interactions between the target and receptor that bring about chemical changes such as the production of a new molecule, the release of heat, the flow of electrons or changes in pH or mass.

The transducer is a device that needed to convert a wide range of physical, chemical or biological signals into an electrical signal with high sensitivity and reliability and plays an important role in the signal detection process of the biosensor. There are five main types of biosensors determined by the nature of the biological signal that is transduced.

Optical biosensors detect light produced, reflected, transmitted or absorbed during the interaction with the sensing element. Optical sensing platforms employ various methods, including refractive index change monitoring, absorption, and spectroscopic-based measurements. Potentiometric biosensors detect the production of an electrical potential due to a change in the distribution of electrons through bonding or adsorption etc. Acoustic wave biosensors are based on the detection of a change in mass from the reaction of a biological component of the sensor and the target. Amperometric biosensors can detect the movement of electrons due to the presence of redox reactions. Calorimetric biosensors detect heat that is absorbed or released from the reaction of the sensor and the target.

Transducer signals may then be processed through microelectronics and a data processor, amplified, interpreted and then displayed. Processed signals and results can also be recorded and historical data that is acquired over time can be compiled and displayed.

However, there are limitations to both the recognition elements and transducer devices that are used in the wide variety of biosensors that have been developed. For example, the biological material that is selected for use on the recognition element may denature under environmental conditions (e.g. pH, temperature or ions) or produce a faint or contaminated biological signal.

Some commercial microarrays rely on the detection of labeled target molecules. However, the labeling process complicates the sample preparation, detection process, and also may change the molecule's binding properties, which may compromise the detection accuracy and reliability of the biosensor.

Transducer platforms may also have inherent detection, conversion or sensitivity limitations in the conversion of the biological signals into electrical signals. For example, fluorescence detectors may have difficulty detecting low intensity emissions or low numbers of bound targets may not produce a physical change that is detectable by the transducer.

Accordingly, there is a need to develop more efficient, sensitive and reliable transduction and detection technologies. There is also a need for new diagnostic devices and assays that have quick response times, that are label free, are highly sensitive and selective and are inexpensive to produce and operate.

BRIEF SUMMARY

The present technology provides a sensing platform utilizing surface plasmon resonance based transduction and optical detection. The sensor structure of the platform has a low index support, a high contrast grating, a low index spacer and a thin metal film with a target recognition element. The sensing platform has a sensor or array of sensors, a light source and an optical detector.

The surface plasmon resonance based sensor uses surface plasmon waves (electromagnetic waves) to detect changes on the surface of the sensor when the target interacts with a target recognition element. The binding of the target with a receptor will induce changes in the refractive index, which changes the resonance wavelength of the plasmon wave on the sensor surface, and that change is used to measure or observe the reaction.

The sensor design has four important parts. The first part is a high contrast grating (HCG) that is used to phase-match the input optical beam and the surface plasmon polariton (SPP) mode that will in turn excite the SPP mode. The HCG grating refers to a one-dimensional or two-dimensional array of sub-wavelength-sized, high-refractive-index dielectric structures placed in nearly periodic fashion surrounded by a low refractive index medium. The second important part is the thin film of metal with a surface that supports the SPP mode and a recognition element. The top of the metal surface is where sensing is performed with interactions of a target with the recognition element. The third is a spacer material with a relatively low refractive index that is disposed between the metal surface layer and the HCG grating structure. The fourth is a support substrate which is placed below the HCG that is used to support the sensor structure and can provide a flexible or a rigid platform.

The typical sensor has a recognition element associated with one side of the metal thin film and a low index spacer on the under side of the metal film. The spacer separated the metal layer from the high contrast grating surrounded with low refractive index material and preferably incorporated on a flexible support substrate. The high contrast grating assists the excitation of surface plasmon polariton and improves the quality factor of the optical resonance. The target recognition element of the sensor includes the metal thin film and a selected target interaction scheme such as antibody-antigen, enzyme-substrate or nucleic acid fragments etc. For example, the sensor takes advantage of the high specificity and affinity of antibodies to directly detect unlabeled analytes without requiring sample purification or enrichment, competitive immunoassay set-ups, or the use of labeled reagents.

The preferred sensing platform can have two sensing configurations: The first uses a light source with a relatively broad emission spectrum, such as a wavelength-swept laser or LED, that can be used to excite the SPP. A spectrometer can then be used to record reflection spectrum. A shift of resonance wavelength is used for quantitative detection. The second uses a light source with fixed wavelength or a narrow bandwidth laser as light source near the sensor resonance wavelength and a photodetector can be used to record the reflection intensity. In this embodiment a change on or above the surface will shift the resonance wavelength and bring the intensity change which can be detected visually or with a mechanical detector.

Traditional SPP sensors are expensive and difficult to use because it is very challenging to launch an optical beam and excite the in-plane propagating SPP mode efficiently either with free space or fiber optics, due to large mode mismatches. By comparison, the addition of a high contrast grating with the present technology makes it possible to couple light in and out efficiently using a surface-normal configuration of free space or fiber optics with large tolerances. Consequently, it is possible to develop sensors that are cost-effective and detect efficiently with high sensitivity. In addition, the surface-normal topology facilitates 2D arrays of SPP sensors.

The optical sensor can be adapted for use for with various sensing requirements, such as medical diagnostics, biochemical sensing, gas sensing, and chemical detection etc. For example, the sensor can be used with Lab-on-a-chip micro-fluidic systems, such as medical diagnostics, biochemical sensing, environmental monitoring, industrial process control systems, chemical detection, and food safety detection. The sensor can also be used with hand-held optical sensor systems, such as medical diagnostics, biochemical sensing, environmental monitoring, industrial process control systems, chemical detection, and food safety detection. The sensors can also be used as an accessory for a smart phone, used for medical diagnostics, biochemical sensing, environmental monitoring, industrial process control systems, chemical detection, and food safety detection.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only:

FIG. 3C and FIG. 3D illustrate two dimensional HCG gratings with hexagonal spatial periodicity with circular elements in FIG. 3C and hexagonal elements shown in FIG. 3D. FIG. 3E to FIG. 3G are examples of apodized HCG reflectors configurations to achieve spatial mode engineering.

FIG. 10A is a cross-sectional view of a starting semiconductor wafer with sacrificial layer disposed under the device layer.

FIG. 10B is a cross-sectional view showing the application of a patterned photoresist on the device layer.

FIG. 10C is a cross-sectional view showing the definition of the grating layer with etching.

FIG. 10D is a cross-sectional view showing the removal of the photoresist from the structure of FIG. 10C.

FIG. 10E is a cross-sectional view showing selective etching to remove portions of the sacrificial layer from the structure of FIG. 10D.

FIG. 10F is a cross-sectional view showing the application of a flexible layer to the grating structure of FIG. 10E.

FIG. 10G is a cross-sectional view showing the separation and removal of the flexible layer and grating structure from the structure of FIG. 10F.

FIG. 10H is a cross-sectional view showing the application of a thin film flexible material on top of the separated grating structure of FIG. 10G.

FIG. 10I is a cross-sectional view showing the application of a thin film of meta to produce a surface plasmon polariton waveguide on top of the flexible material of the separated grating structure of FIG. 10H.

DETAILED DESCRIPTION

Referring more specifically to the drawings, for illustrative purposes, embodiments of the sensor platform are generally shown.

Several embodiments of the technology are described generally in FIG. 1 through FIG. 14B to illustrate the apparatus and methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
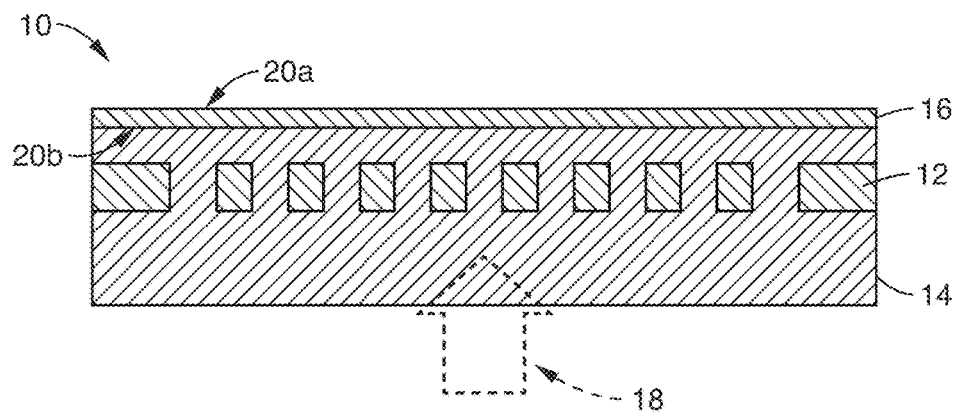
FIG. 1 is a schematic cross sectional view of an optical sensor according to one embodiment of the technology (not to scale).

Turning now to FIG. 1, one preferred embodiment of a surface plasmon polariton based sensor device 10 according to the technology is generally described. The optical sensor device illustrated in the FIG. 1 has at least one high contrast grating 12 disposed within a carrier material such as low refractive index base support structure 14 below a thin film of metal 16 on the top surface of the sensor 10 structure. Sensing is performed on the top surface 20a of the thin film of metal 16. Flexible carriers 14 are preferably used to support the sensor structure 10 and to provide a flexible platform. However, rigid low index materials may also be used as a support structure 14 in some embodiments.

The grating 12 is used to do phase matching between the input light 18 and surface plasmon polariton at the interface of the bottom side 20b of the metal layer 16 and a spacer or part of the support 14. It can also form a cavity with the metal layer to enhance the surface plasmon excitation efficiency. The high contrast grating 12 assists the excitation of surface plasmon polariton and improves the quality factor of the optical resonance. Surface plasmon polariton (SPP) is a transverse magnetic surface electromagnetic excitation that propagates along the underside surface 20b of metal layer 16. The mode field is concentrated on the bottom metal surface of the metal layer 16 providing a sensitive detection to the change on or above the metal surface 20a. The high contrast grating (HCG) has been shown to possess the extraordinary property of being a broadband reflector with high Q resonance. Here the HCG is used to assist in the excitation of surface plasmon polariton and then the concentrated optical field near the metal surface is used to detect the chemical, gas and biosensing.

The sensor illustrated in FIG. 1 is shown working under surface normal input light. However, with different HCG designs, various working angles (from surface normal to large glancing angle) can also be utilized.

The high contrast grating 12 is a single layer of subwavelength grating with the grating bars made with high index material that is fully surrounded by the low index materials of the support 14. In FIG. 1, there is a separation between the grating layer and metal layer that is filled with a spacer material 14. The spacer thickness or gap can vary from 0 to several micrometers. In addition, the spacer material does not need to be the same low index material used with support 14 and can be a separate layer. The spatial periodicity of the grating can be designed as one dimensional or two dimensional, as shown in FIG. 2A to FIG. 2F and FIG. 3A to FIG. 3G.

Figure 2A:
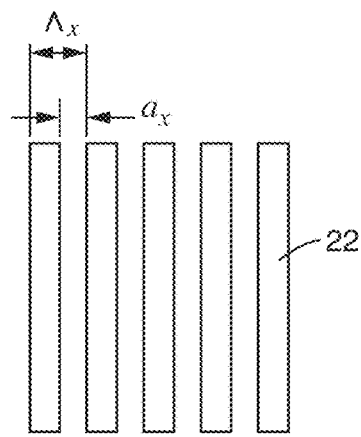
FIG. 2A to FIG. 2C are top view of one dimensional HCG grating patterns.
Figure 2B:
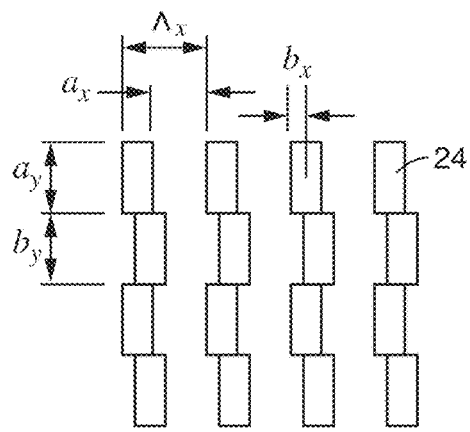
Figure 2C:
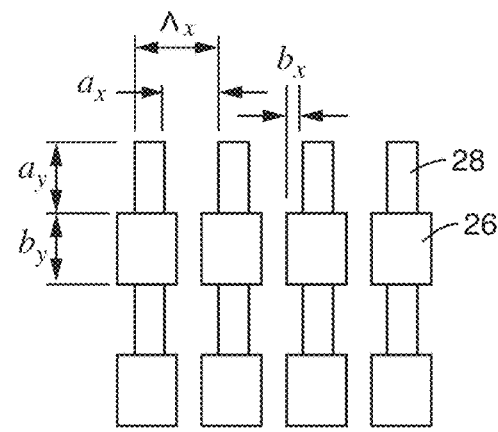

FIG. 2A to FIG. 2C are top view illustrations of one dimensional high contrast grating patterns. In the embodiment of FIG. 2A, the grating bars 22 are equally sized and spaced in parallel. The grating bars may also be formed from vertically or horizontally offset elements 24 as shown in FIG. 2B. The grid bars may also be formed from different sized elements such as larger 26 and smaller 28 elements as shown in FIG. 2C.

Figure 2D:
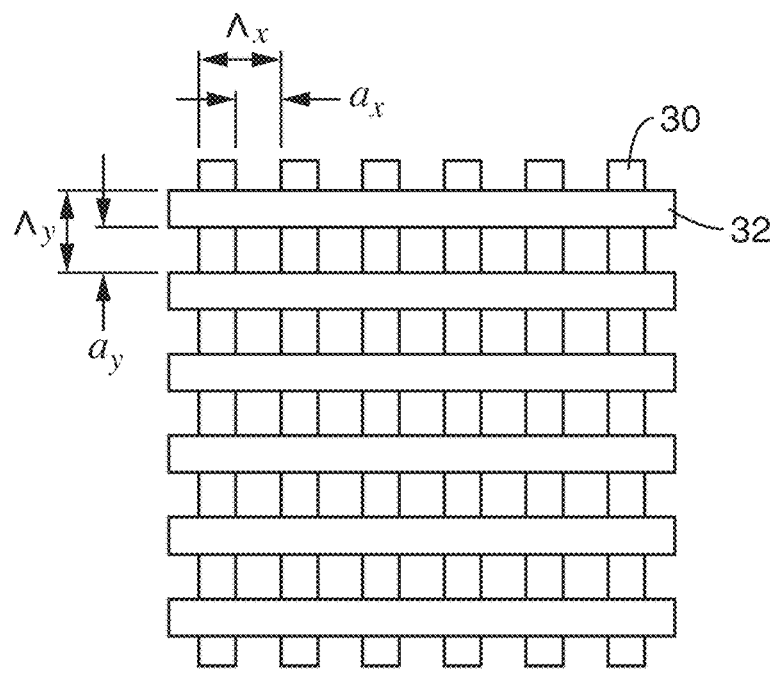
FIG. 2D to FIG. 2F are two dimensional HCG patterns according to various embodiments of the technology.
Figure 2E:
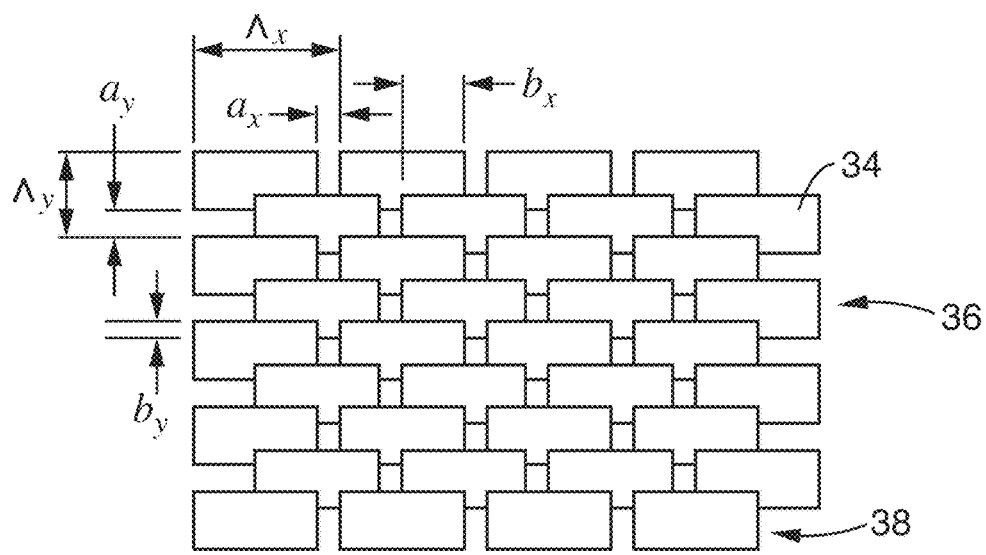
Figure 2F:
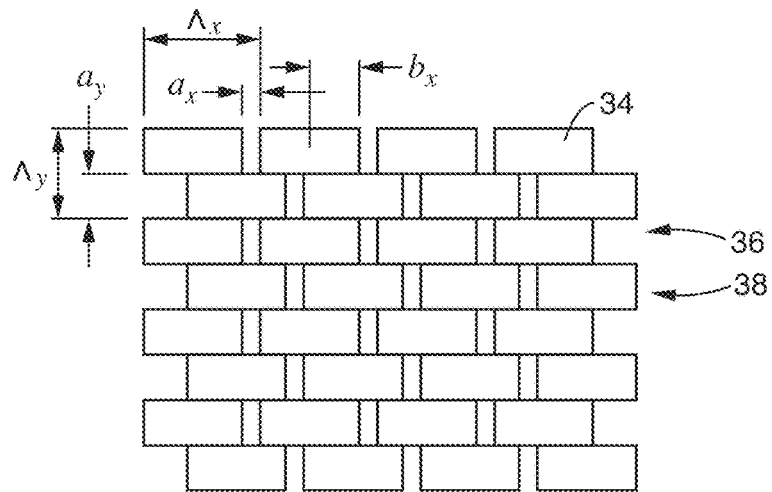

The gratings illustrated in FIG. 2D to FIG. 2F are two dimensional high contrast grating patterns according to various embodiments of the technology. The two dimensional grating of FIG. 2D is formed from column elements 30 and row elements 32 set in a simple grid pattern. More complicated grid patterns such as that shown in FIG. 2E can be produced with overlapping elements 34 that are placed in offset rows 36 and 38. Similarly, the elements 34 can be placed in offset rows 36 and 38, but the elements 34 do not overlap as shown in FIG. 2F.

The one dimensional patterns of FIG. 2A to FIG. 2C are generally polarization sensitive. The two dimensional patterns of FIG. 2D to FIG. 2F can be either symmetric and polarization insensitive or asymmetric and polarization sensitive. $\Lambda_x$, $\Lambda_y$ are the grating periods in the two directions and $a_x$, $a_y$, $b_x$, $b_y$ and the thickness of the grating elements are the other design parameters.

Besides the rectangular elements in the connected and non-connected domain shown in FIG. 2A to FIG. 2F, elements with other shapes can also be used. These shapes are preferably placed at a selected subwavelength periodicity, where the period is less than or close to the wavelength of interest.

Figure 3A:
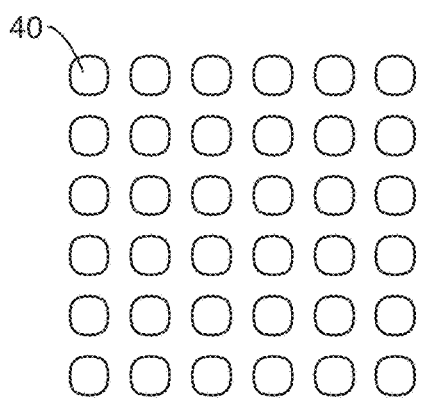
FIG. 3A to FIG. 3G depict two dimensional gratings with different high index grating bar shaped elements, such as round-corner rectangle seen in FIG. 3A, and circular shape seen in FIG. 3B that are placed in a square shaped array.
Figure 3B:
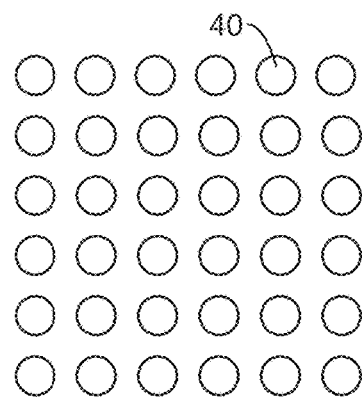
Figure 3C:
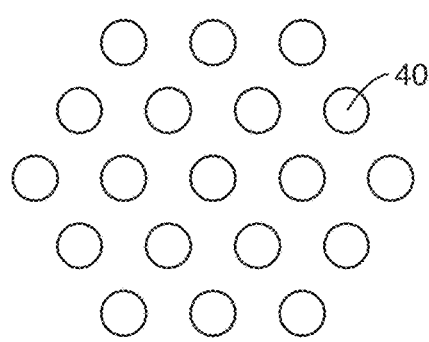
Figure 3D:
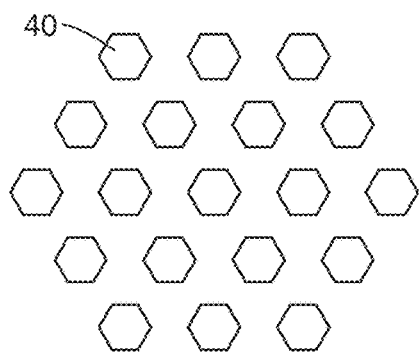

FIG. 3A to FIG. 3G depict two dimensional gratings with different high index grating bar shaped elements 40, such as round-corner rectangle shapes seen in FIG. 3A, and circular shaped elements seen in FIG. 3B that have been placed in a square shaped array. FIG. 3C and FIG. 3D illustrate two dimensional HCG gratings with hexagonal spatial periodicity with circular elements 40 in FIG. 3C and hexagonal elements 40 shown in FIG. 3D. The grating 12 can also follow other periodical grids in addition to the square and hexagonal grid illustrated in FIG. 3A through FIG. 3D.

Figure 3E:
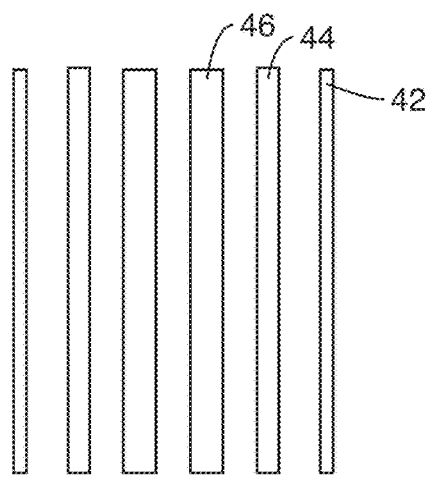
Figure 3F:
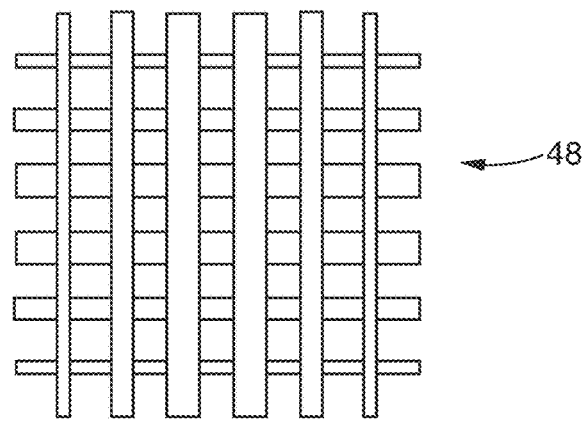
Figure 3G:
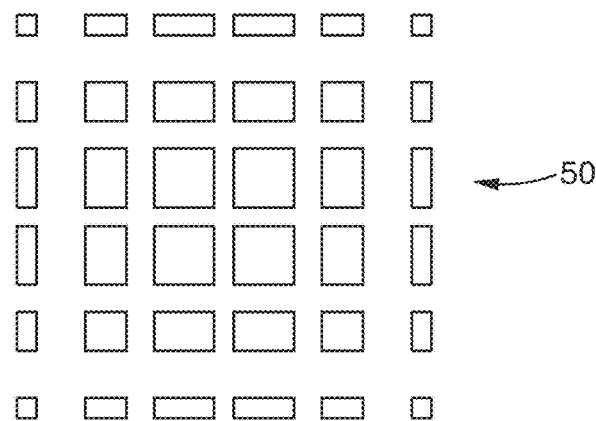

FIG. 3E illustrates an embodiment of a pattern of grating 12 with high index grating bar shapes of different widths. The grating has a repeating pattern of a narrower bar 42, a wider bar 44 and the widest bar 46. In this embodiment, the grating 12 is made to provide the spatial mode by apodizing the grating to be non-periodic. In the grating 48 shown in FIG. 3F the pattern of FIG. 3E of vertical bars of varying widths is overlaid with the same pattern of horizontal bars. Another example of a one dimensional or two dimensional apodized structures are illustrated in the pattern 50 of FIG. 3G. The period and duty cycle can be changed at each unit period of the high contrast grating.

Figure 4:
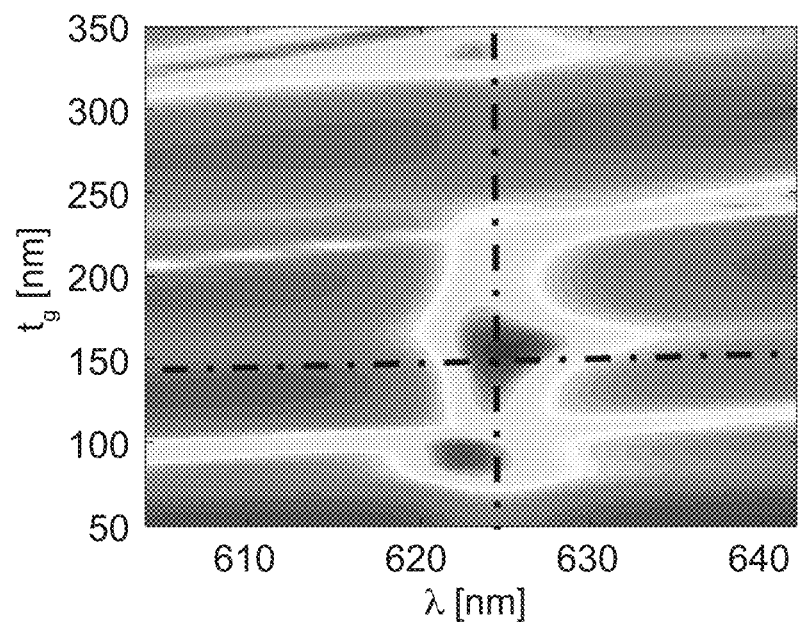
FIG. 4 is a graph of reflection as function of working wavelength and grating thickness. Period was chosen to be 600 nm in this case and duty cycle was 50%. Vertical dotted line represents the effective index of SPP mode.
Figure 5:
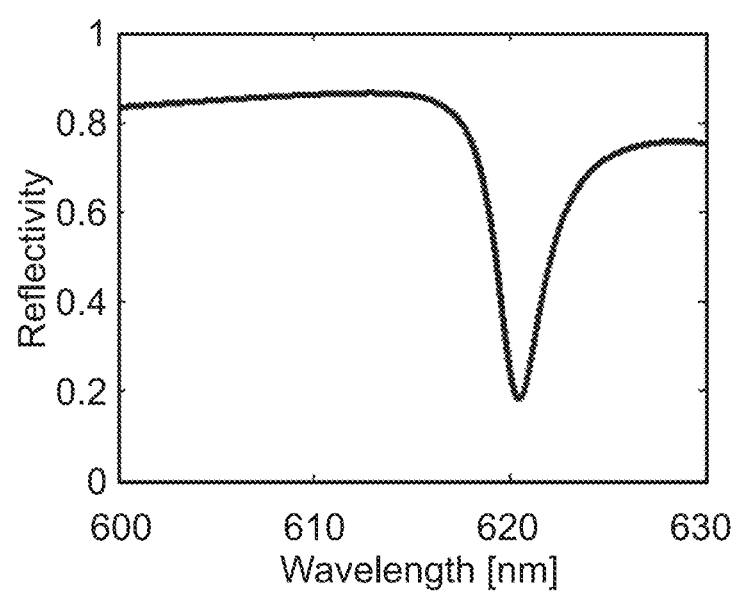
FIG. 5 is a graph of a reflection spectrum for a sensor design with period=600 nm, duty cycle 50% and grating thickness=149 nm representing the horizontal dotted line of the graph of FIG. 4.

The design principle of the optical sensor can be illustrated using FIG. 4. In the graph of FIG. 4, the reflection is plotted as a function of grating thickness and operation wavelength. The period of the grating is chosen when $\lambda/\Lambda = n_{eff}$, where $\lambda$ is the working wavelength, $\Lambda$ is the grating period and $n_{eff}$ is the effective index of the SPP mode. The thickness of the grating elements can be chosen from the graph of FIG. 4 to optimize the resonance effect. The period was chosen to be 600 nm in this case and duty cycle was 50%. The vertical dotted line on the graph of FIG. 4 represents the effective index of SPP mode. FIG. 5 is a graph of a reflection spectrum for a sensor design with period=600 nm, duty cycle 50% and grating thickness=149 nm representing the horizontal dotted line of the graph of FIG. 4.

Once the SPP mode is excited, small changes of on or above the top surface 20 of layer 16 will be reflected in a wavelength shift of the reflection spectrum. The detectable changes could also be changes of surrounding refractive index, thickness of material attached to the surface, etc.

Figure 6:
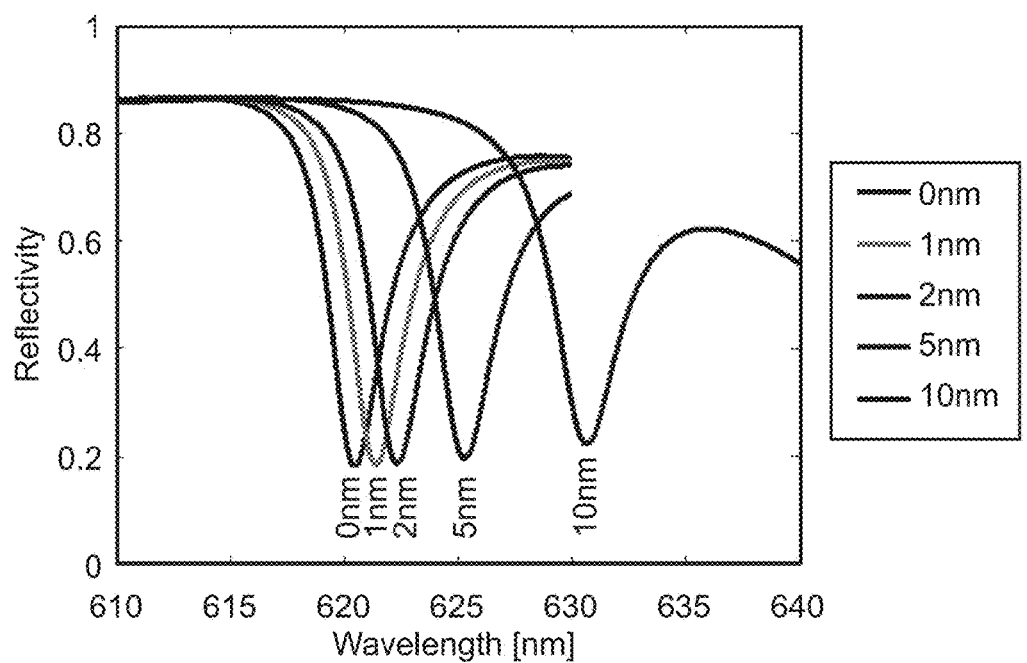
FIG. 6 is a graph of reflection spectra with different layer thickness of material that is attached to the surface as indicated.
Figure 7:
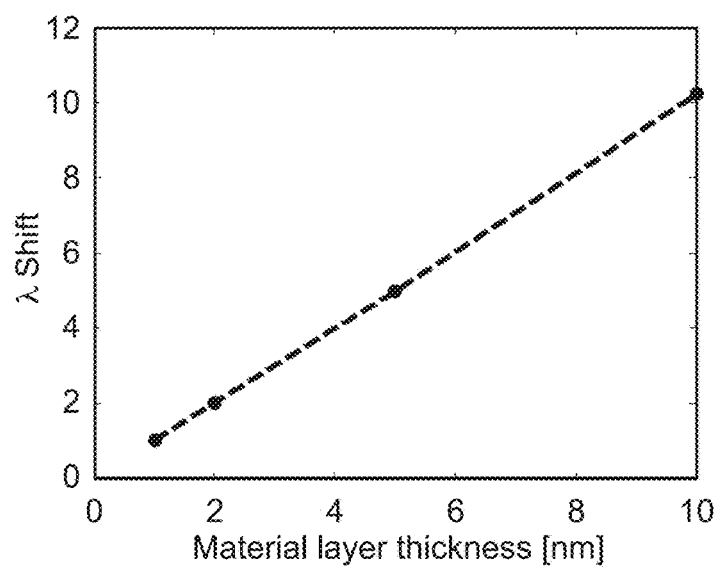
FIG. 7 is a graph of the resonance wavelength as function of material layer thickness that is attached to the metal surface.

FIG. 6 is a graph of reflection spectra with different layer thickness of material that is attached to the grating and metal surfaces and FIG. 7 is a graph of the resonance wavelength as a function of material layer thickness that is attached to the grating and metal surfaces. FIG. 6 and FIG. 7 show the sensor response to the thickness of material attached to the surface.

Figure 8:
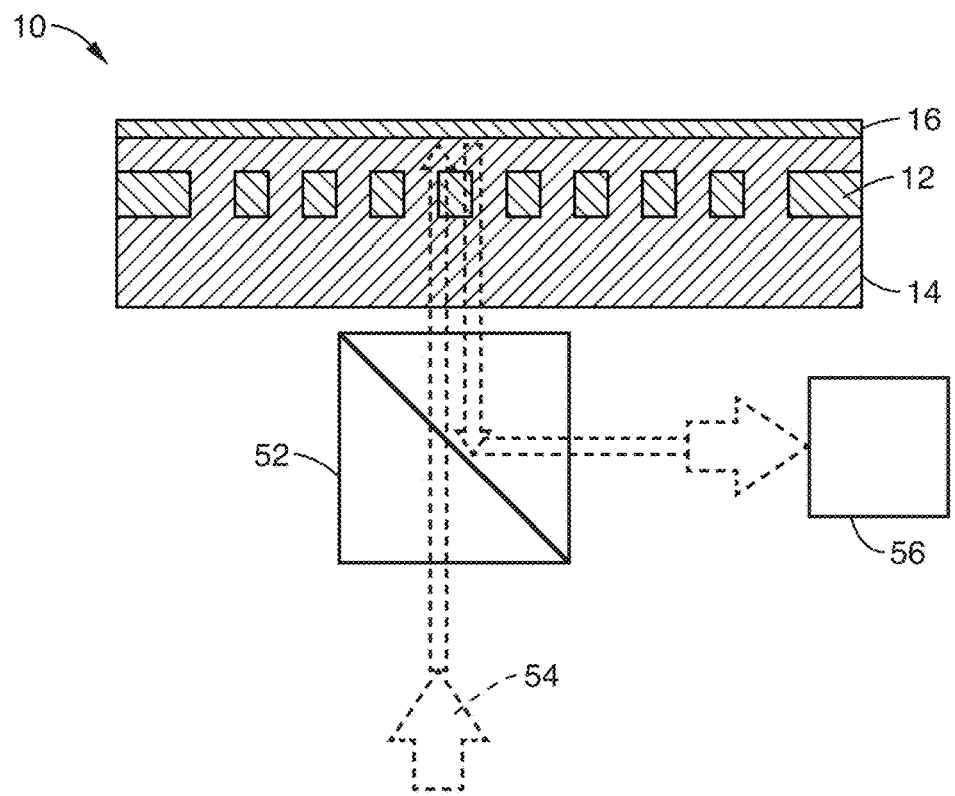
FIG. 8 is a schematic side view of a sensor configuration with a broadband source and spectrometer according to one embodiment of the technology.

FIG. 8 is an illustration of a sensing configuration using a broadband light source 54 as the input light and a spectrometer detector 56 to record the reflection spectrum. In this configuration, the broadband source 54 is used to excite SPP by being directed through the beam splitter 52 and through the sensor support 14 and grating 12 to the bottom surface of metal layer 16. The beam is reflected out through the sensor structure and through the beam splitter 52 to the spectrometer 56. The whole reflection spectrum is typically recorded over time. A shift in the resonance wavelength is used for quantitative detection.

Figure 9:
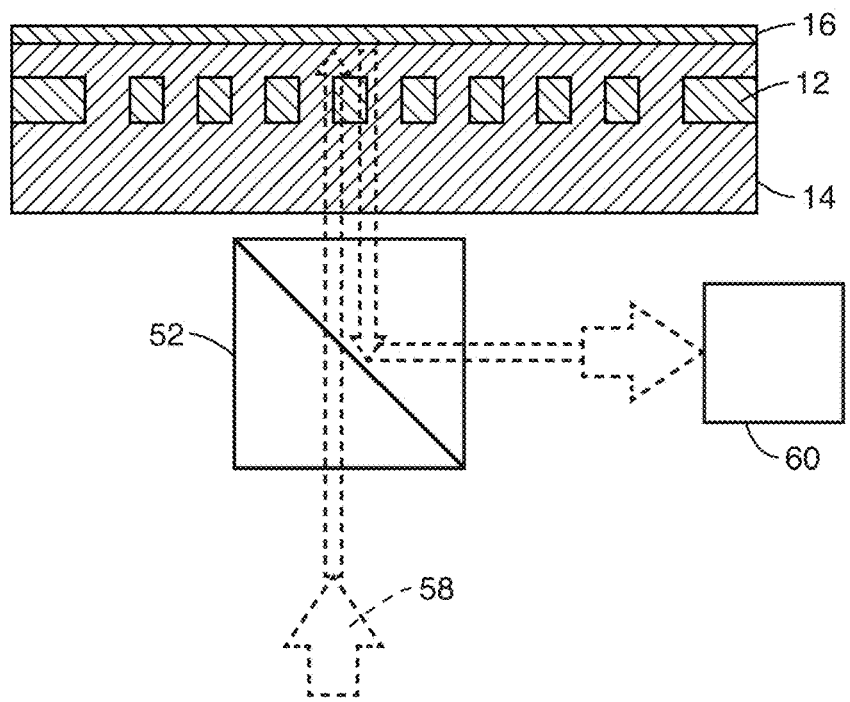
FIG. 9 is a schematic side view of a sensor configuration with laser source and photodetector according to another embodiment of the technology.

FIG. 9 is an illustration of a sensing configuration using a narrow bandwidth source (i.e. laser) 58 as the light source and a photodetector 60 to record the reflection intensity. In this configuration, a narrow band source 58 may be used as the light source and the wavelength is chosen to be near the sensor resonance wavelength. The light 58 is directed through beam splitter 52 and through the structure and grating to the bottom surface and interface between the metal layer and the low index material. The reflection is directed back out through the beam splitter 52 to the photodetector 60. The photodetector 60 is used to record the reflection power or other characteristics. Change on or above the surface 16 will shift the resonance wavelength and bring a detectable intensity change at the detector.

One embodiment of the fabrication process 62 of a sensor with a flexible support and single grating is illustrated in FIG. 10A through FIG. 10I. FIG. 10A through FIG. 10I is a sequence of schematic cross-sectional views showing sequential process steps for the formation of a sensor according to one embodiment of the technology as shown in FIG. 1.

Figure 10A:
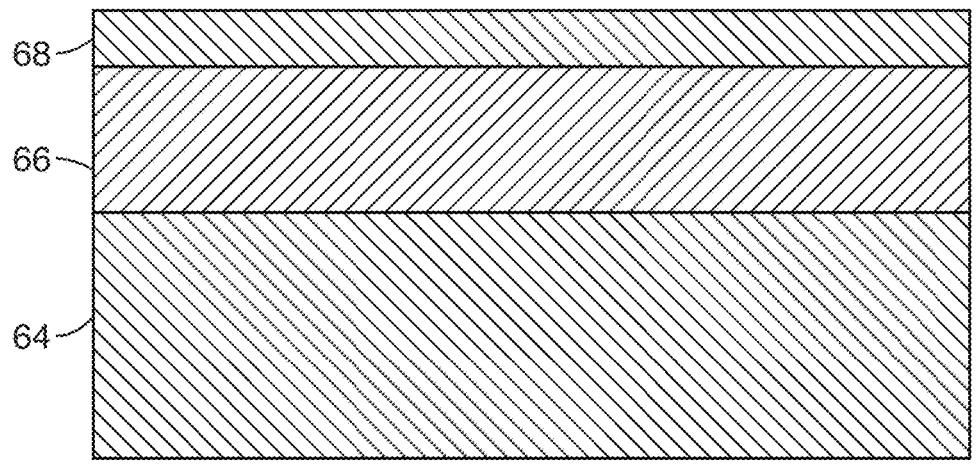
FIG. 10A through FIG. 10I is a sequence of schematic cross-sectional views showing sequential process steps for the formation of a sensor according to one embodiment of the technology as shown in FIG. 1.

The process starts with a semiconductor wafer with a substrate 54 and a sacrificial layer 66 under a device layer 68. The sacrificial layer 66 can be selectively etched to suspend portions of the patterned device layer 68. One common structure with such a configuration is the silicon-on-insulator wafer as shown in FIG. 10A. The wafer has a silicon device layer on top of a buried oxide layer, which serves as the sacrificial layer that can be selectively removed with hydrofluoric acid. However, a silicon-on-insulator wafer is preferred, other material combinations with selective etching capabilities can also be utilized, for instance, InP/AlGaInAs, GaAs/AlGaAs, etc.

Figure 10B:
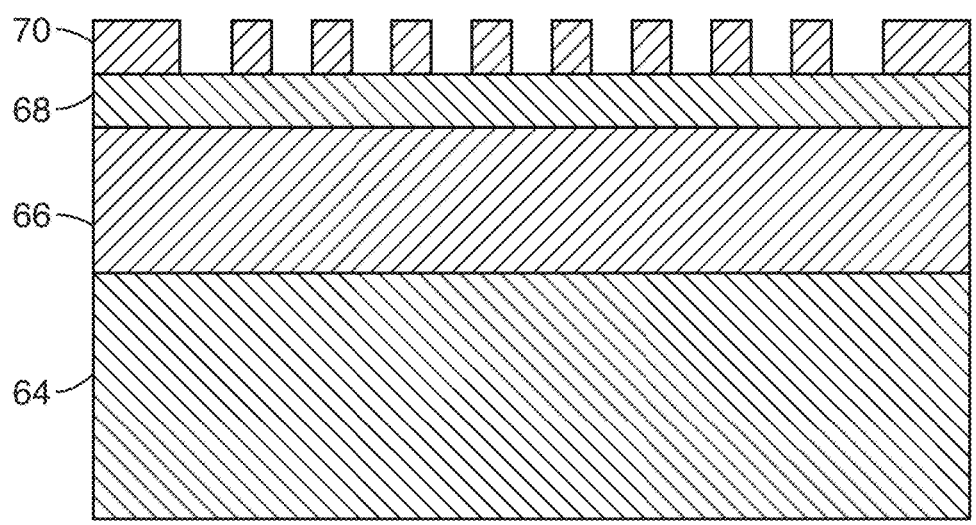

As seen in FIG. 10B, the device layer 68 has a photoresist layer 70 applied to the top surface that is patterned by conventional lithography techniques. The feature size is directly related to the target optical resonance wavelength of the device.

Figure 10C:
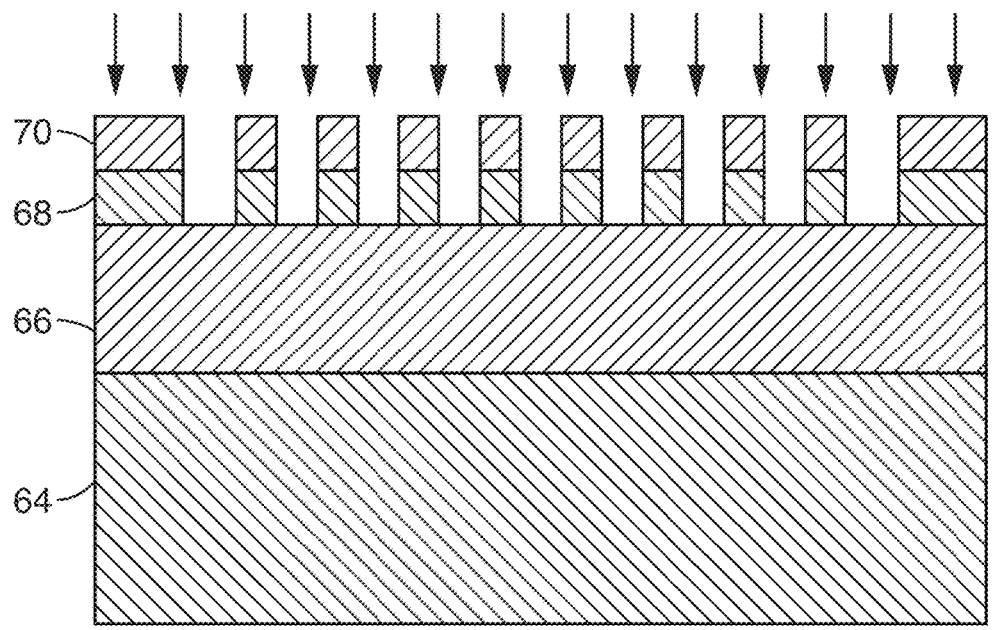

Following the lithography step, an etching step is performed to etch away the exposed area of the device layer 68, as illustrated in FIG. 10C. The pattern of the high contrast gratings are therefore defined with transferring the pattern from the photoresist layer to the semiconductor layer.

Figure 10D:
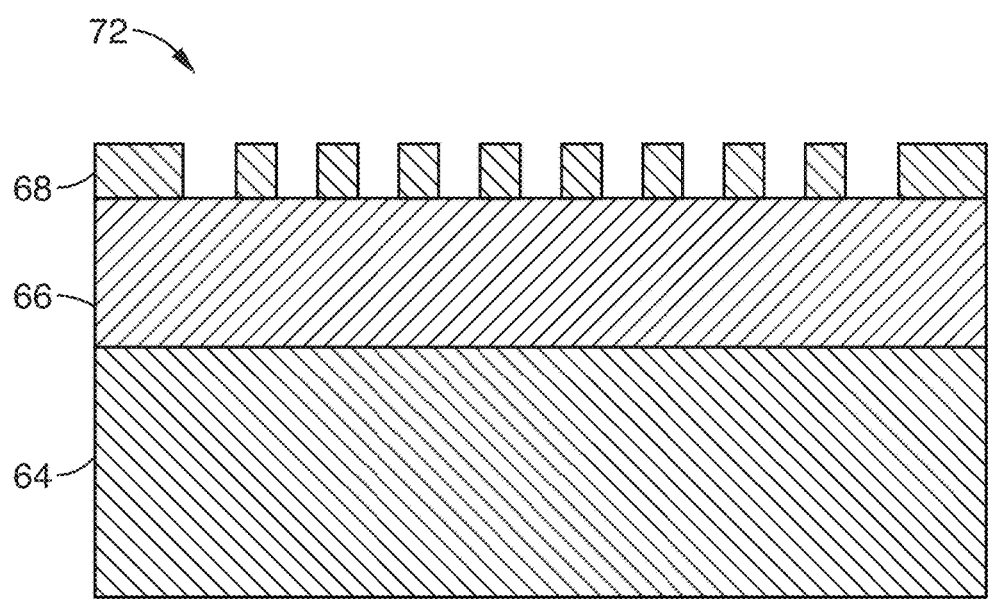

FIG. 10D illustrates the cross section after the photoresist is removed. The device layer 68 now has a pattern 72 that exposes the sacrificial oxide layer 66 to etching. In order to facilitate the transfer of the grating to another substrate, the HCG structure needs to be released from the original rigid substrate structure.

Figure 10E:
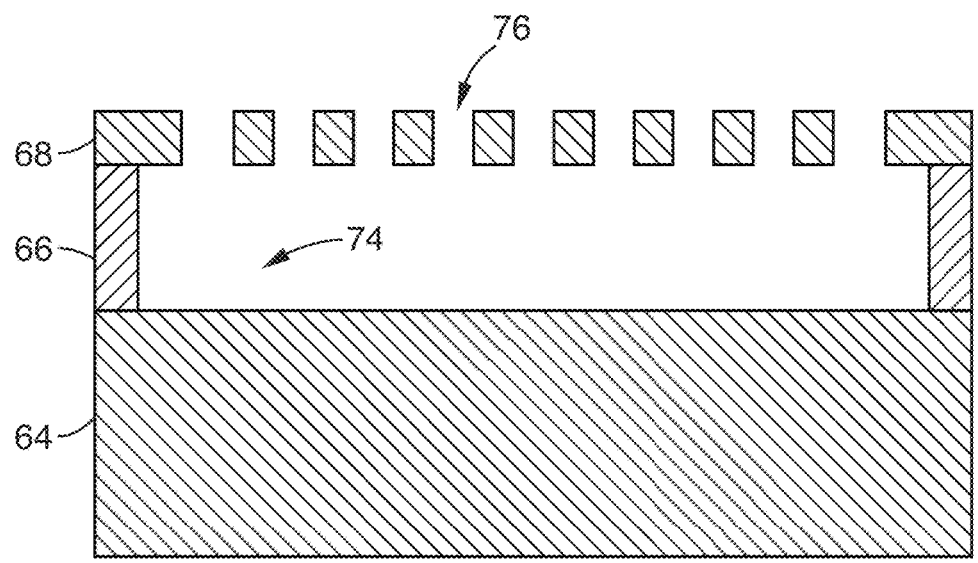

As shown in FIG. 10E, the sacrificial layer 66 under the patterned grating layer 68 is selectively etched through the openings 76 in the pattern to form a gap 74 under the device layer, thereby suspending the patterned grating bars over the gap 74.

Figure 10F:
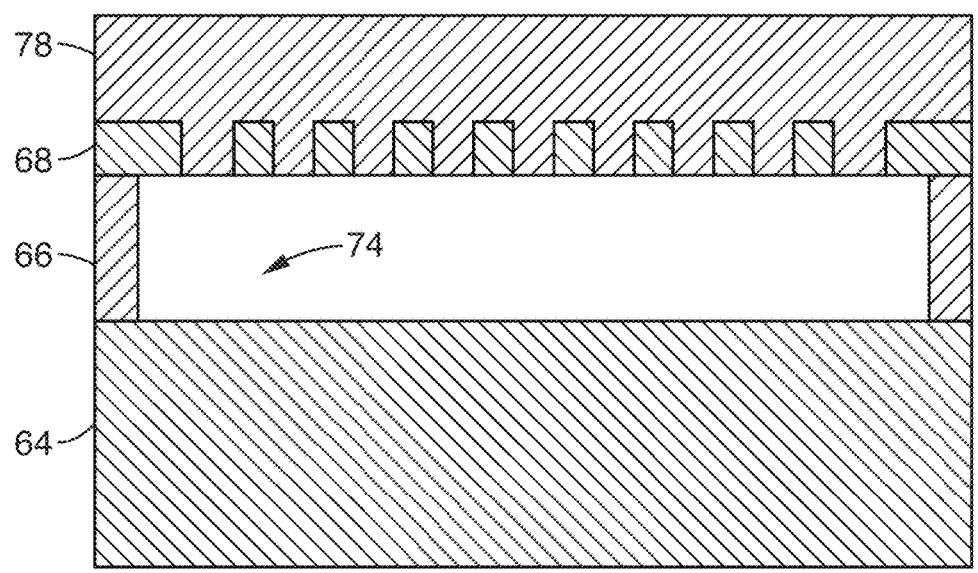

Then a support layer 78 of flexible material such as polydimethylsiloxane (PDMS) is applied to patterned grating bars and the device layer 68 to fill the openings 76 as shown in FIG. 10F. The suspended patterned grating bars will attach to the surface of the flexible support layer 78. The patterned grating 68 is transferred to the flexible substrate from the wafer by peeling off the flexible support layer 78 from the rigid etched wafer. The separated structure is shown in FIG. 10G that has the patterned device layer 68 embedded in the flexible support layer 78 and an open surface 80 that once faced the interior of gap 74 of FIG. 10E and FIG. 10F.

Figure 10G:
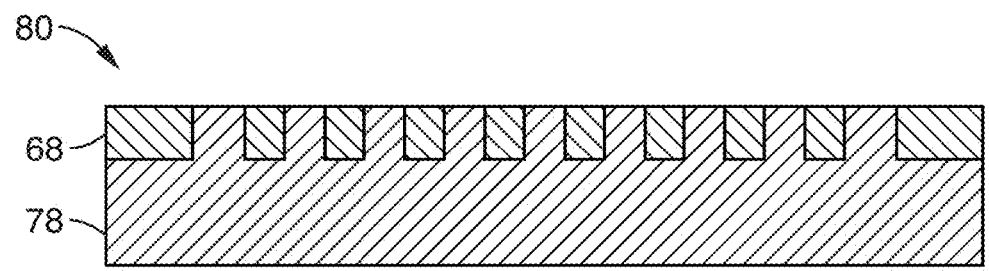
Figure 10H:
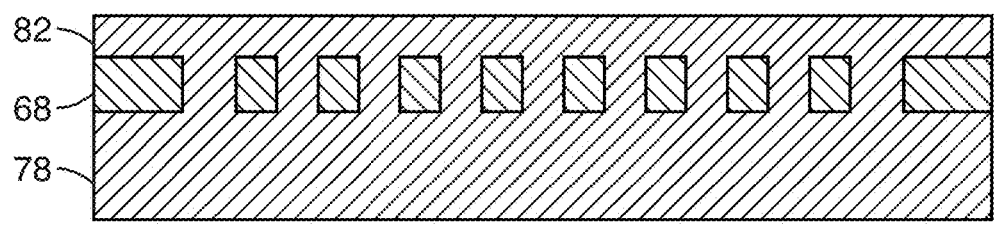

After the grating 68 is transferred to the flexible carrier 78, another thin polymer layer 82 is coated on top of the surface 80 to produce the structure shown in FIG. 10G. The thickness of this layer can be adjusted up or down. However, the preferred thickness of this thin flexible (PDMS) layer is in the range from approximately 10 nm to approximately 1000 nm. It can be achieved by the spin coating process with the PDMS diluted in hexane. The thickness of layer 82 can be controlled by varying the dilution ratio and the spin coating speed and time, for example.

Figure 10I:
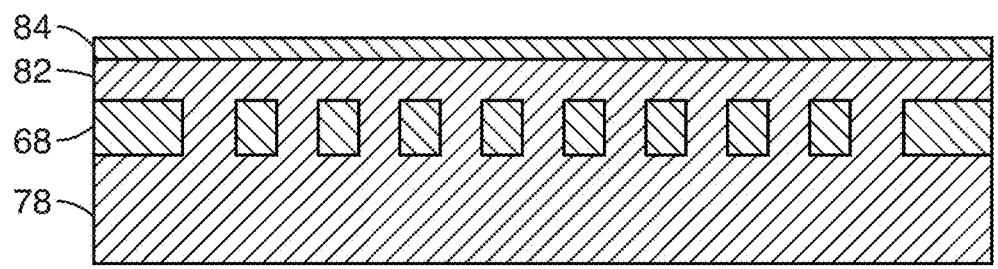

In the last step, the surface plasmon polariton sensor structure has a metal layer applied fabricated by metal evaporation or some other conventional method, as shown in FIG. 10I. The final structure has a metal layer that has a top surface and a bottom surface that is part of an interface between the metal layer 84 and the low index polymer layer 82 of a desired thickness. The top surface of the metal layer 84 can be functionalized with one of several different types of target sensing schemes.

Each of these target sensing schemes will produce a change in the observed reflection/transmission spectrum or reflection/transmission intensity and the surface plasmon polariton waves and resonance upon binding or other interaction with the designated target.

Surface plasmon resonance (SPR) is a phenomenon that is observed when light is reflected off of thin films of metal. Surface Plasmon Polaritons (SPP) are electromagnetic excitation waves that propagate at the surface of the metal layer. Any changes in the status of either the dielectric or metal materials will alter the characteristics of the surface waves that are observed such as a variation in the propagation constant of the surface plasmon waves. Essentially, a change on or above the metal surface will change the surface plasmon wave and results in intensity change or the spectral shift of the reflected light that is detected.

Figure 11:
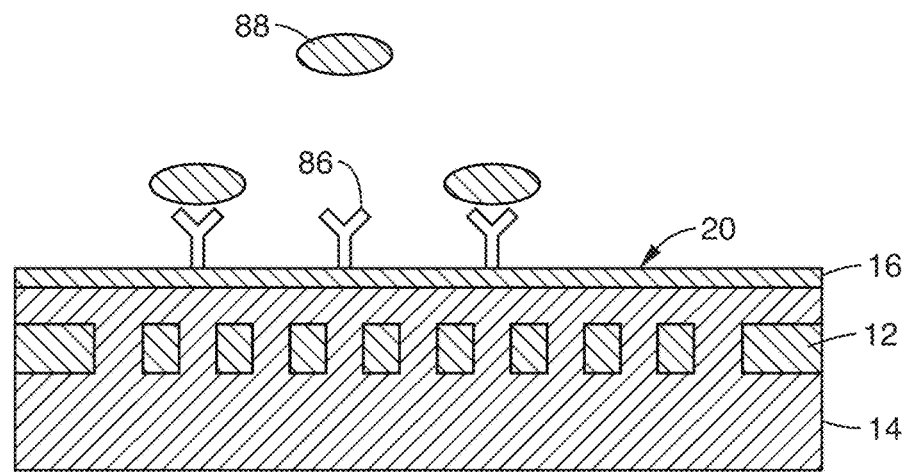
FIG. 11 is a schematic cross sectional view of an optical gas sensor with a surface functionalized with gas acceptors according to one embodiment of the technology.

Accordingly, the sensor can detect changes when the target analyte interacts with the recognition element of the sensor that is disposed on the surface of the metal layer by the changes observed in the reflected/transmitted light. For example, the sensors can be adapted to gas, biological and chemical sensing schemes. A gas sensor is generally illustrated in FIG. 11 using the device structure shown in FIG. 8 or FIG. 9. Acceptor molecules 86 are first attached to the sensor surface 20, and then gas molecule 88 will be captured by the acceptor 86 with high specificity. After binding, the reflection spectrum will then shift according to the amount of gas molecules 88 are captured by the acceptors 86.

Figure 12:
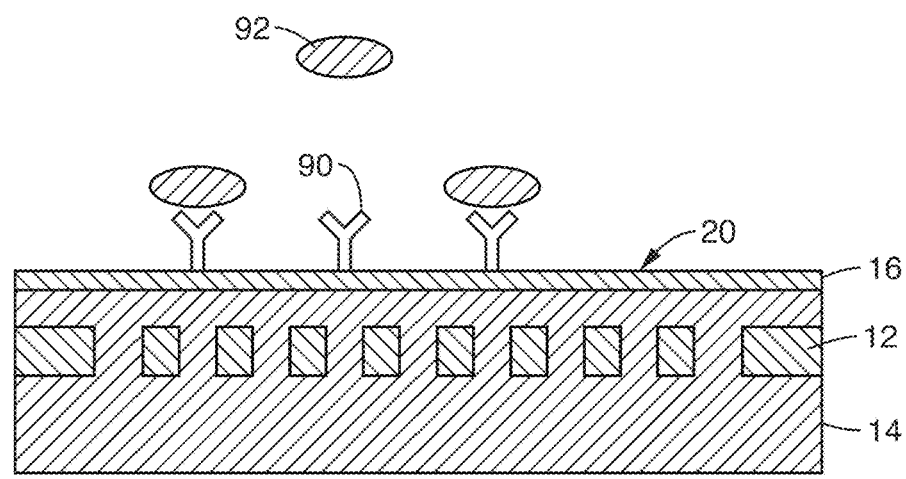
FIG. 12 is a schematic cross sectional view of an optical biological sensor with a surface functionalized with antibodies according to another embodiment of the technology.

Similarly, the sensors can be adapted for biosensing as illustrated schematically in FIG. 12. In this case, antibodies 90 can be applied to the sensor surface 20 to detect the corresponding antigen molecule 92 from a sample. The antibody-antigen binding will produce a detectable change in the reflection/transmission of the sensor.

Figure 13:
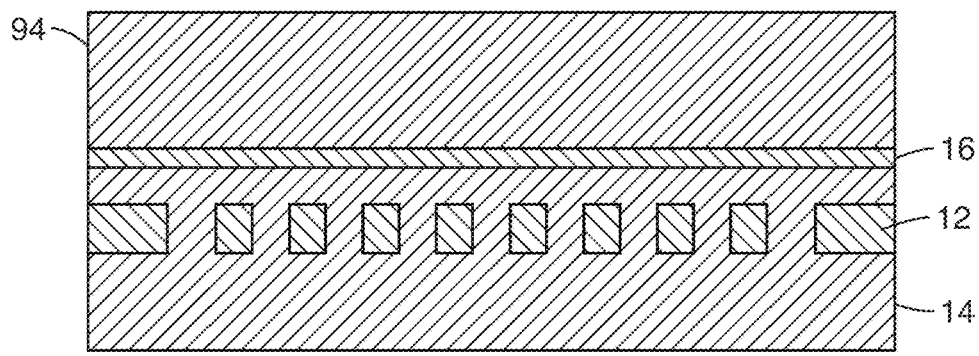
FIG. 13 is a schematic cross sectional view of an optical chemical sensor with a surface functionalized with antibodies according to another embodiment of the technology.

For the chemical sensing case illustrated in FIG. 13, the fact that different chemicals having different refractive indexes is utilized. And the index difference will also shift resonance wavelength accordingly. In this case, the surface 20 of the sensor is coated with a suitable chemical sensing material 94. Reaction of the material 94 with a target chemical will shift the resonance wavelength or otherwise cause a detectable change in intensity.

The creation of a flexible sensor of the present technology permits the adaptation of the sensing system to a variety of diagnostic applications. For example, a catheter bacteria detector is shown schematically in FIG. 14A and FIG. 14B. The optical sensor can be used to achieve low cost catheter bacteria detection. Because such a structure can be fabricated on a flexible substrate, it can be wrapped to form a tube. With standard tubing connectors, the sensor tubing section can be connected in series with the ordinary plastic tubing. With the sensing mechanism described above, the resonance wavelength is sensitive to the antibody-antigen reaction on the metal surface, leading to the sensitive detection of the bacteria in the tubing.

Figure 14A:
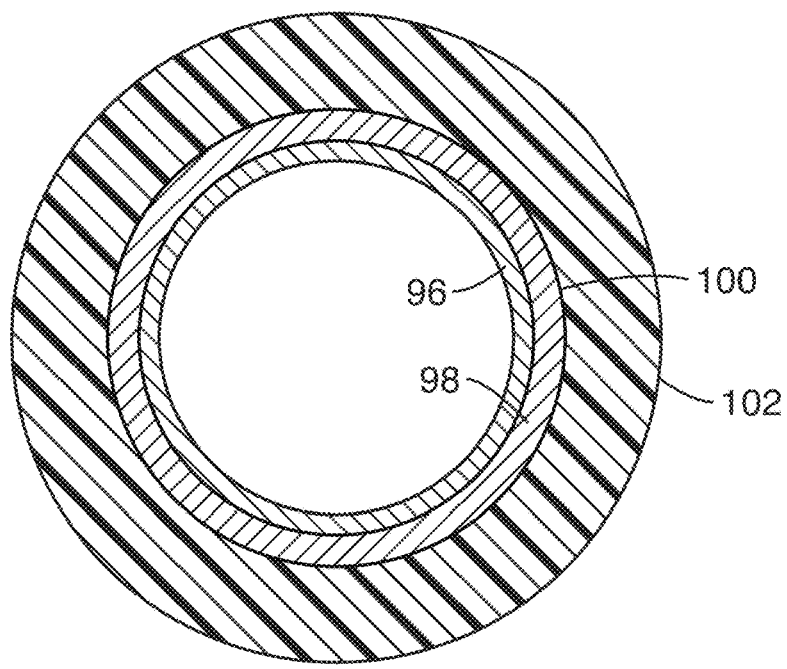
FIG. 14A is a cross-sectional view and FIG. 14B is a perspective view of a tubular sensor design according to the technology.
Figure 14B:
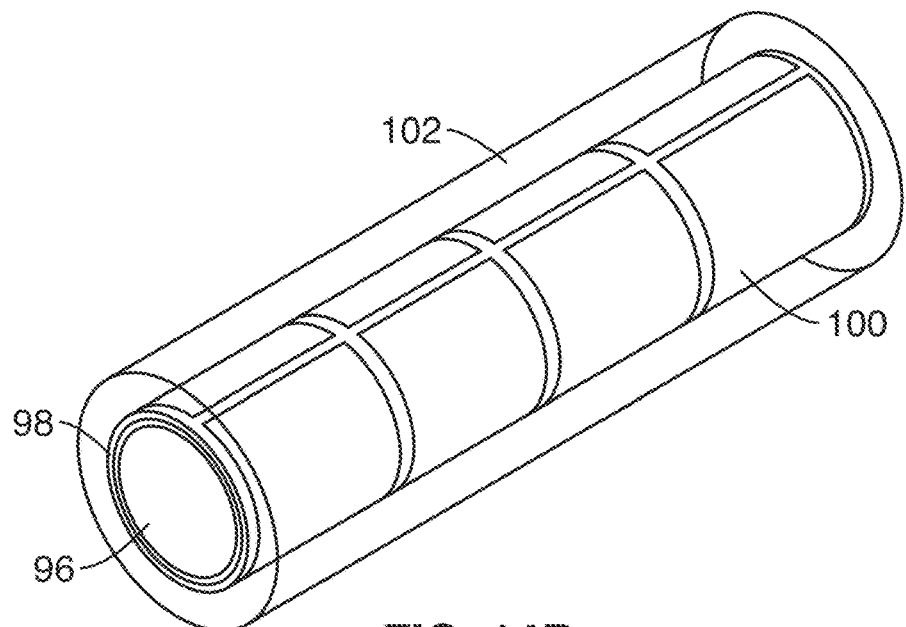

In the embodiment shown in FIG. 14A and FIG. 14B, the sensor can be rolled into a tube or multiple sensors can be formed into a tube. In the cross-section of 14A, the functionalized metal layer 96 forms the interior of the tube. The polymer layer 98 surrounds the inner metal layer 96. A flexible outer support layer 100 covers and incorporates the grating layer 100. The outer support layer 102 is preferably transparent to allow the use of an external light source or layer 102 can incorporate light sources and detector elements.

Such devices can be used to detect hospital-acquired infections (HAI) that are infections developed within a hospital environment. Over 1.7 million HAIs are estimated in the United States every year, resulting 99,000 deaths. Catheter-related infections, which are caused by the presence of the bacteria in the catheters, can lead to very severe consequences. The catheter-related bloodstream infection is one of the most frequent, lethal and costly complications of the venous catheterization. Attributed to the increase in invasive medical devices and procedures, immunocompromised patients and an overall increase in elderly patients, the death rate of catheter-related infection has been increase in the recent decades. Therefore, inexpensive detection of intact bacteria flowing through the catheter is critical for reducing the infection, resulting less complications for the current procedures and overcoming the obstacles for exploring the advanced treatments.

The invention may be better understood with reference to the accompanying examples, which are intended for purposes of illustration only and should not be construed as in any sense limiting the scope of the present invention as defined in the claims appended hereto.

EXAMPLE 1

In order to demonstrate the capabilities of the sensor platform of the present technology, a sensor device with the structure illustrated in FIG. 1 was fabricated. The carrier was made from PDMS (or other low index material with index<1.45) and the grating layer was silicon 220 nm in thickness. However, Si can be replaced by other high index material (with index>1.45). The metal thin film layer was made from gold and was 50 nm thick. The space between the grating and the thin metal film was 200 nm with a PDMS spacer. However, the separation between the metal layer and the grating can vary from 0 nm to sub-micrometers in thickness.

In this example, reflected light was collected and analyzed to obtain the information of changes on the sensor surface. The input light goes through the grating layer and excites surface plasmon at the metal surface. Changes in the metal surface were visualized in the form of changes of reflected or transmitted signal. Here, the refractive index of the analyte on top of the sensor metal film surface was changed and the corresponding change in the reflection light was monitored.

The fabricated apparatus was used to observe the spectral shift as a function of the analyte index change. Reflection spectrum shifts by 16 nm with index change of 0.15. The spectral shift was captured with a spectrometer. It can also be interpreted as color change, which can be visualized by naked eye without the use of an additional instrument. In this case, the transmitted color center shifted to the deep red side when the index of the analyte increased. The fabricated apparatus was used to observe the spectral shift for different analytes on the sensor surface as function of analyte refractive index.

EXAMPLE 2

To further demonstrate the sensor platform capabilities, the sensor was demonstrated to operate in another mode where the reflected intensity (at a fixed wavelength or a fixed bandwidth) served as an indicator of sensor surface change. The reflected (transmitted) signal intensity change can be captured by photo detector. It can also be visualized as brightness change without additional instrument. The intensities at a fixed wavelength and at a fixed bandwidth were compared to obtain information of sensor surface change. In this example, the intensity of the reflected (transmitted) light was monitored and it indicated the change of sensor surface. Intensity change percentage as function of surface analyte refractive index showed that the intensity changed by 31% with analyte index change by 0.15.

From the description herein, it will be appreciated that that the present disclosure encompasses multiple embodiments which include, but are not limited to, the following:

1. An optical sensor device, comprising: (a) a carrier material; (b) a metal layer adjacent the carrier material; (c) a high contrast grating embedded in the carrier material and positioned adjacent the metal layer; (d) wherein the metal layer has a sensor surface; (e) wherein the metal layer has an excitation surface along an interface between the carrier material and the metal layer, along which surface plasmon polaritons travel when the excitation surface is excited by a light source; and (f) wherein the high contrast grating provides phase matching between the light source and the surface plasmon polaritons to couple photons from the light source to the surface plasmon polaritons for excitation.

2. The sensor device of any preceding embodiment, further comprising a target recognition element on the sensor surface of the metal layer.

3. The sensor device of any preceding embodiment, wherein the surface plasmon polaritons are responsive to a change on or above the sensor surface of the metal layer resulting from interaction between a target material and the target recognition element.

4. The sensor device of any preceding embodiment, wherein optical waves from the light source are reflected by the interface surface of the metal layer and wherein the high contrast grating focuses the reflected optical waves for detection of the target material.

5. The sensor device of any preceding embodiment, wherein the carrier material comprises a flexible carrier.

6. The sensor device of any preceding embodiment, wherein the high contrast grating has one-dimensional or two-dimensional spatial periodicity.

7. The sensor device of any preceding embodiment, wherein the carrier material comprises a low refractive index dielectric material.

8. The sensor device of any preceding embodiment, wherein the high contrast grating comprises a high refractive index material.

9. The sensor device of any preceding embodiment, wherein the sensor device is a component of a sensor selected from the group of sensors consisting of a biosensor, a gas sensor, a chemical sensor, and a catheter bacteria detector.

10. A sensor apparatus for an optical detection platform, the apparatus comprising: (a) a low index of refraction sensor support; (b) a high contrast grating coupled to the support; (c) a thin metal film; (d) a low refractive index spacer separating the high contrast grating from a lower surface of the thin metal film; and (e) one or more target recognition elements disposed on an upper surface of the thin metal film.

11. The apparatus of any preceding embodiment, wherein the sensor support is a flexible material comprising polydimethylsiloxane (PDMS).

12. The apparatus of any preceding embodiment, wherein the high index grating comprises a plurality of separate spaced apart segments of high refractive index material surrounded by low refractive index materials.

13. The apparatus of any preceding embodiment, wherein the spacer is a low index polymer layer having a thickness in the range of 10 nm to 1000 nm.

14. The apparatus of any preceding embodiment, wherein the target recognition elements couple with the metal layer is an element selected from the group of an antibody, a gas acceptor and a chemical receptor.

15. An optical detection platform apparatus, comprising: (a) a light source; (b) a sensing element, comprising: (i) a low index of refraction sensor support; (ii) a high contrast grating coupled to the support; (iii) a thin metal film; (iv) a low refractive index spacer separating the high contrast grating from a lower surface of the thin metal film; and (v) one or more target recognition elements disposed on an upper surface of the thin metal film; and (c) an optical detector; (d) wherein the metal layer has an excitation surface along an interface between the spacer material and the lower surface of the metal layer, along which surface plasmon polaritons travel when the excitation surface is excited by the light source; and (e) wherein an association of a target with the target recognition elements alters the surface plasmon polariton and a signal detected by the optical detector.

16. The apparatus of any preceding embodiment, wherein the light source comprises a broadband light source and the optical detector comprises a spectrometer.

17. The apparatus of any preceding embodiment, wherein the light source comprises a narrow band laser light source and the optical detector comprises a photodetector.

18. The apparatus of any preceding embodiment, wherein the sensor support is a flexible material comprising polydimethylsiloxane (PDMS).

19. The apparatus of any preceding embodiment, wherein the high index grating comprises a plurality of separate spaced apart segments of high refractive index material surrounded by low refractive index material.

20. The apparatus of any preceding embodiment, wherein the high contrast grating comprises a subwavelength grating with the grating bars made with a silicon high index material.

21. The apparatus of any preceding embodiment, wherein the spacer is a low index polymer layer dielectric material having a thickness in the range of 10 nm to 1000 nm.

22. The apparatus of any preceding embodiment, wherein the target recognition elements couple with the metal layer is an element selected from the group of an antibody, a gas acceptor and a chemical receptor.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An optical sensor device, comprising:
   (a) a carrier material;
   (b) a metal layer adjacent the carrier material; and
   (c) a high contrast grating embedded in the carrier material and positioned adjacent the metal layer;
   (d) wherein said metal layer has a sensor surface having a target recognition element;
   (e) wherein said metal layer has an excitation surface along an interface between the carrier material and the metal layer, along which surface plasmon polaritons travel when the excitation surface is excited by a light source;
   (f) wherein the high contrast grating provides phase matching between the light source and the surface plasmon polaritons to couple photons from the light source to the surface plasmon polaritons for excitation;
   (g) wherein the surface plasmon polaritons are responsive to a change on or above the sensor surface of the metal layer resulting from interaction between a target material and the target recognition element; and
   (h) wherein optical waves from the light source are reflected by the interface surface of the metal layer and wherein the high contrast grating focuses the reflected optical waves for detection of the target material.

2. The sensor device of claim 1, wherein the carrier material comprises a flexible carrier.

3. The sensor device of claim 1, wherein the high contrast grating has one-dimensional or two-dimensional spatial periodicity.

4. The sensor device of claim 1, wherein the carrier material comprises a low refractive index dielectric material.

5. The sensor device of claim 1, wherein the high contrast grating comprises a high refractive index material.

6. The sensor device of claim 1, wherein the sensor device is a component of a sensor selected from the group of sensors consisting of a biosensor, a gas sensor, a chemical sensor, and a catheter bacteria detector.

* * * * *